United States Patent [19]
Persson

[11] Patent Number: 5,601,610
[45] Date of Patent: *Feb. 11, 1997

[54] CURRENT LEAKAGE PREVENTION CIRCUIT FOR AN EXTERNAL DEFIBRILLATOR

[75] Inventor: Eric Persson, Minnetonka, Minn.

[73] Assignee: SurvivaLink Corporation, Minneapolis, Minn.

[*] Notice: The term of this patent shall not extend beyond the expiration date of Pat. No. 5,484,452.

[21] Appl. No.: 565,365

[22] Filed: Nov. 30, 1995

Related U.S. Application Data

[63] Continuation of Ser. No. 41,006, Mar. 31, 1993, Pat. No. 5,484,452.
[51] Int. Cl.$^6$ ...................................................... A61N 1/39
[52] U.S. Cl. ................................................. 607/5; 607/63
[58] Field of Search ................................... 607/5, 6, 7, 63

[56] References Cited

U.S. PATENT DOCUMENTS 5,484,452  1/1996  Persson ........................................ 607/5

Primary Examiner—William E. Kamm
Assistant Examiner—Scott M. Gettzow
Attorney, Agent, or Firm—Patterson & Keough, P.A.

[57] ABSTRACT

An external defibrillator high voltage circuit with a leakage prevention circuit. The high voltage circuit includes first and second output terminals configured for electrical interconnection to electrodes, first and second charge supply terminals configured for interconnection to a charging voltage supply, and a plurality of capacitors. Charging semiconductor switches which are responsive to charge control signals electrically interconnect the capacitors to the charge supply terminals in a parallel circuit to charge the capacitors. Discharging semiconductor switches which are responsive to discharge control signals electrically interconnect the capacitors in a series circuit between the output terminals to generate defibrillation pulses. The discharging switches include at least two switches interconnected to each other at a leakage shunting node and in a series circuit between one of the capacitors and the second output terminal. A leakage shunting switch electrically interconnects the leakage shunting node to the first output terminal when switched to a closed state to reduce leakage currents through the patient when defibrillation pulses are not being produced. Charge dump semiconductor switches discharge the capacitors when the switches are switched to an electrically closed state. A voltage sensing circuit is coupled to and detects the voltage at the leakage shunting node. The voltage sensing circuit causes the charge dump switches to be switched to the electrically closed state to discharge the capacitors when the detected voltage is greater than a predetermined level.

22 Claims, 3 Drawing Sheets

CURRENT LEAKAGE PREVENTION CIRCUIT FOR AN EXTERNAL DEFIBRILLATOR

REFERENCE TO RELATED APPLICATION

This application is a continuation of commonly assigned and U.S. application Ser. No. 08/041,006, filed Mar. 31, 1993 now U.S. Pat. No. 5,484,452, and entitled "Current Leakage Prevention Mechanism For Use In A Defibrillator Circuit."

BACKGROUND OF THE INVENTION

1. Field of the Invention

This invention relates to medical therapeutic apparatus. More particularly, this invention relates to electronic circuitry for use in an external defibrillator apparatus. The apparatus of this invention provides an improved, safer defibrillator.

2. Description of the Related Art

The external defibrillator is a well recognized and important tool for resuscitating cardiac arrest patients. Defibrillation of the human heart is accomplished by applying an electrical waveform to the cardiac muscle with appropriate electrodes, causing the cessation of rapid uncoordinated contractions of the heart (fibrillation) and restoration of normal beating of the heart.

In the past, defibrillators have utilized various circuitry in an attempt to minimize leakage of current to the patient during charge up. Current leakage is of particular interest in defibrillator circuitry which utilizes semiconductor components for use in switching. However, prior art circuitry has significant limitations and shortcomings. Despite the need in the art for an external defibrillator apparatus and circuitry therefor which overcomes the limitations and problems of the prior art, none insofar as is known has been proposed or developed. Accordingly, it is an object of the present invention to provide a defibrillator apparatus and circuit therefor which overcomes the limitations and shortcomings of the prior art. Particularly, it is an object of this invention to provide an improved defibrillator apparatus which is reliable, durable, and effective at delivering defibrillating charges to the body of a patient. Another object of this invention is to provide defibrillation circuitry which minimizes current leakage to a patient during charge-up. A specific object of this invention is to provide a current leakage attenuation system for circuitry which charges a plurality of capacitors in parallel and discharges them in series utilizing a plurality of semiconductor switches.

SUMMARY OF THE INVENTION

The present invention is an external defibrillator high voltage circuit which includes a current leakage prevention circuit. One embodiment of the high voltage circuit includes first and second output terminals configured for electrical interconnection to electrodes, and first and second charge supply terminals configured for interconnection to a charging voltage supply. The circuit also includes at least one capacitor for storing electrical energy and at least one charging switch. The charging switch(es) is responsive to charging control signals, and electrically interconnects the capacitor(s) to the charge supply terminals to charge the capacitor(s) when switched to an electrically closed state. A plurality of discharging switches are responsive to discharge control signals and electrically interconnect the capacitor(s) between the first and second output terminals to produce defibrillation pulses when switched to an electrically closed state. The discharging switches include at least two switches interconnected to each other at a leakage shunting node and in a series circuit between the capacitor and the second output terminal. A leakage shunting switch is electrically interconnected between the leakage shunting node and the first output terminal to electrically interconnect the leakage shunting node to the first output terminal when switched to an electrically closed state, thereby reducing leakage currents through a patient when defibrillation pulses are not being produced. The leakage shunting semiconductor switch electrically isolates the leakage shunting node from the first output terminal when defibrillation pulses are produced.

Another embodiment of the invention includes a charge dump circuit having one or more charge dump semiconductor switches in a charge dump current flow path. The charge dump semiconductor switch(es) is responsive to charge dump control signals and simultaneously discharges the capacitor(s) when the charge dump semiconductor switch(es) is switched to an electrically closed state. A voltage sensing circuit is coupled to and detects the voltage at the leakage shunting node. The voltage sensing circuit causes the charge dump semiconductor switch(es) to be switched to the electrically closed state when the detected voltage is greater than a predetermined level.

DESCRIPTION OF THE PREFERRED EMBODIMENT

Figure 1:
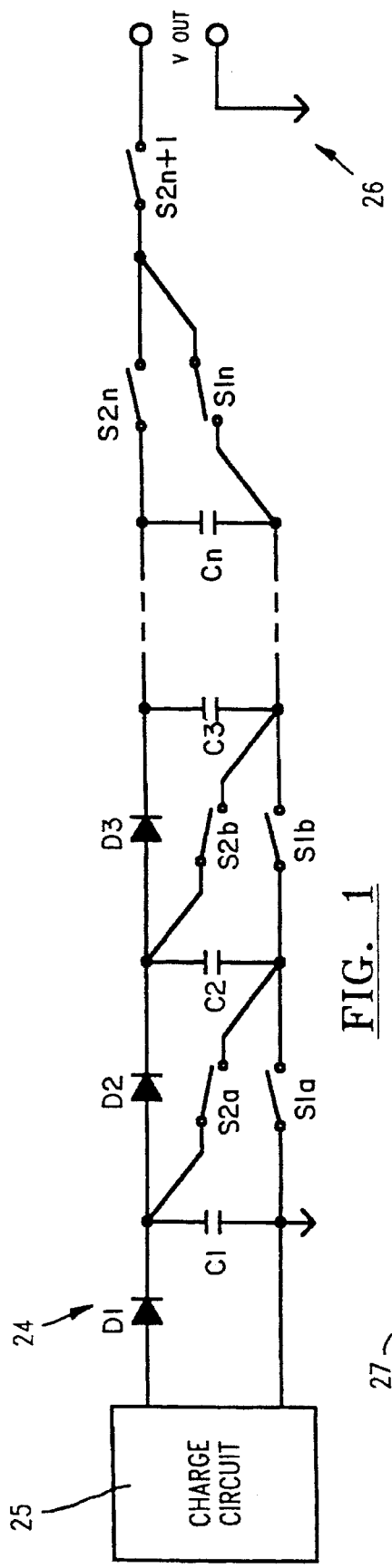
FIG. 1 is a simplified schematic diagram of one embodiment of the defibrillator circuit of the present invention.

Referring to FIG. 1, a basic embodiment of circuitry 24, of the present invention, for a defibrillator is shown comprising a plurality of semiconductor switch elements S in conjunction with a charging circuit 25 and capacitors C. A plurality of 400 to 1200 V semiconductor based components, for example, thyristors are utilized to control switching from charge and discharge states in the defibrillator. The circuit 24 comprises a plurality of capacitors C(1–n), preferably six, connected to a charging circuit 25 and selectively in parallel with respect to each other. The capacitor charging circuit 25 is a current limited voltage source. Small, approximately 400 V capacitors are preferably used.. The configuration of the capacitors C in parallel eliminates the voltage imbalance problem inherent in charging electrolytic capacitors in series. For convenience of reference, the electrodes or terminals of capacitors C(1–n) are designated "second" (positive) at the top end of the circuit 24, and "first" (negative) at the bottom end of the circuit 24.

Still referring to FIG. 1, the circuit 24 is constructed and arranged to allow for the charging of the capacitors C(1–n) in parallel and for discharge in series to deliver required high voltage defibrillating shocks. This is accomplished via the utilization of first semiconductor switches S1(a–n) and second S2 (a–n), primarily.

Five switches S1 (a–n) are disposed in series with respect to each other, each individual switch S1n being disposed between the first electrode of each individual capacitor Cn and the first electrode of its adjacent capacitor Cn+1. The first electrode of capacitor C1 is shown to be connected to ground. Six switches S2(a–n) are disposed essentially in series with each other, each individual switch S2n being disposed between the second electrode of each individual capacitor Cn and the first electrode of its adjacent capacitor Cn+1. When switches S1(a–n) are turned on the capacitors C are connected in parallel.

The last switch S2n in the series is shown to be connected between the second electrode of the last capacitor Cn in the circuit 24 and the output section 26 of the circuit 24. When switches S2(a–n) are turned on the capacitors C are now effectively in series, with the sum of their voltage appearing at Vout. Switch S2(n+1) is a redundant output switch which is turned "on at the same time as the preceding switches S2(a–n). At all times except during output, all switches S1 are "on". Therefore, any leakage currents out of switch S2n is shunted to ground through switches S1(a–n). As a result, switch S2(n+1) has essentially no voltage across it. Therefore, minimal leakage current to the patient occurs. Another advantage of this circuit configuration is that it allows for the sensing of EKG signals and for the performance of lead impedance measurements.

A plurality of diodes D(1–n) are connected in series with each other, the anodes of which are disposed towards the capacitor charging circuit 25. Diode D1 is disposed between the charging circuit 25 and the second electrode of capacitor C1. The remaining diodes D2–Dn are disposed between the second electrode of each capacitor Cn and the second electrode of its adjacent capacitor Cn+1. These diodes allow for parallel charging of the capacitors C, and become reversed biased when switches S2(an) are turned on.

In a charge-up state, switches S2 (a–n) are open and switches S1(a–n) are closed. The capacitors C1–n charge in parallel. Switches S1 can be implemented by an optocoupled transistor, such as that shown in FIG. 5 as OP1, for example. No component of this circuit 24 will see a voltage higher than the voltage present on one capacitor C. As a result, where this circuit 24 has six capacitors C and a peak circuit 24 output of approximately 2000 V, no capacitor C will see more than approximately 333 volts. This allows the use of relatively inexpensive components having the same breakdown voltage of approximately 400 V. Each capacitor Cn+1 has one (1) diode drop less voltage than its adjacent capacitor Cn. An additional benefit of this low voltage circuit configuration is that leakage currents, which are inherent in semiconductor components and on the circuit boards, for example, at high voltages, are minimized.

During discharge to a patient, switches S2(a–n+1) are closed and switches S1(a–n) are open. The capacitors C1–n thus discharge in series, delivering current to the patient's heart. Switches S2 can be implemented via a variety of semiconductor means, but a thyristor, triac or transistor are preferred for cost reasons. Triggering of these switches S2(a–n+1) is accomplished via a galvanically isolated circuit. Triggering is preferably accomplished magnetically via gate drive transformers to simultaneously trigger switches S2. An optically coupled SCR or triac may alternatively be used.

Figure 2:
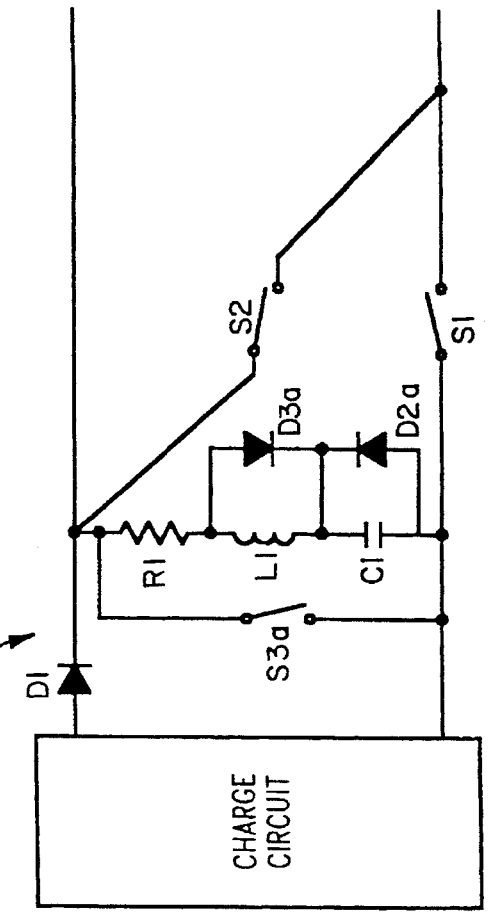
FIG. 2 is a schematic diagram which shows detailed structure for the embodiment shown in FIG. 1.

Referring to FIG. 2, a segment 27 of a preferred circuit embodiment is shown. Current limit and rise time limit in the switches S2 is implemented by placing a resistor R1 and an inductor L1 in series with each capacitor Cn. Additionally, a parallel dump switch S3 is shown added across the network C1/L1/R1 to deliver an appropriate defibrillation waveform with a rapid drop in voltage at a predetermined time. This is particularly important when thyristors, which are difficult to turn off, are utilized in switching. A clamp diode D2(a–n) is added across each capacitor Cn to prevent that capacitor Cn from becoming reverse biased. In addition, a flyback diode D3(a–n) may be included across each inductor Ln if a power transistor, which can be turned off as well as on, is used in the circuit.

Figure 3A:
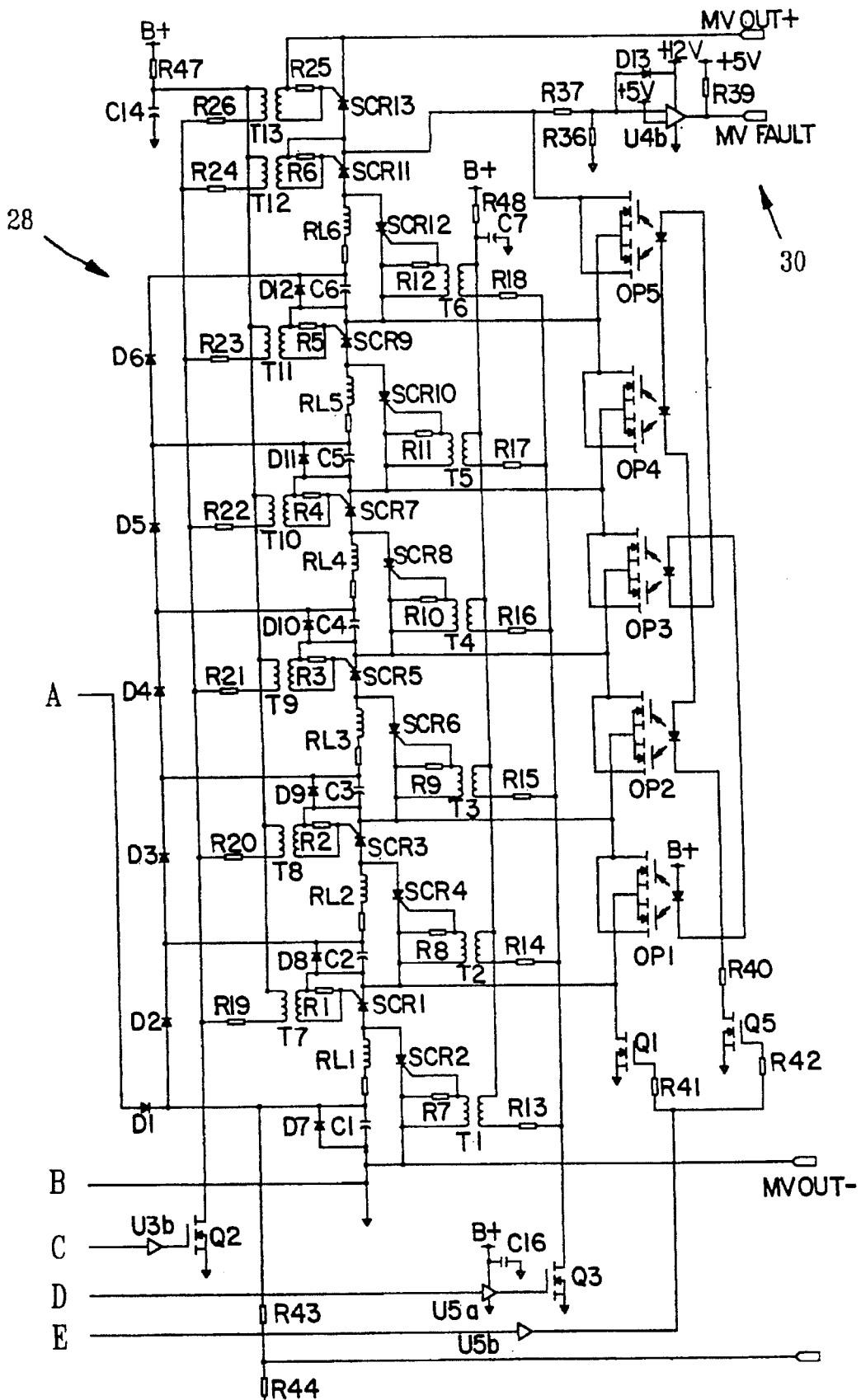
FIG. 3 is a schematic diagram of the most preferred embodiment of the defibrillator circuit of this invention.
Figure 3B:
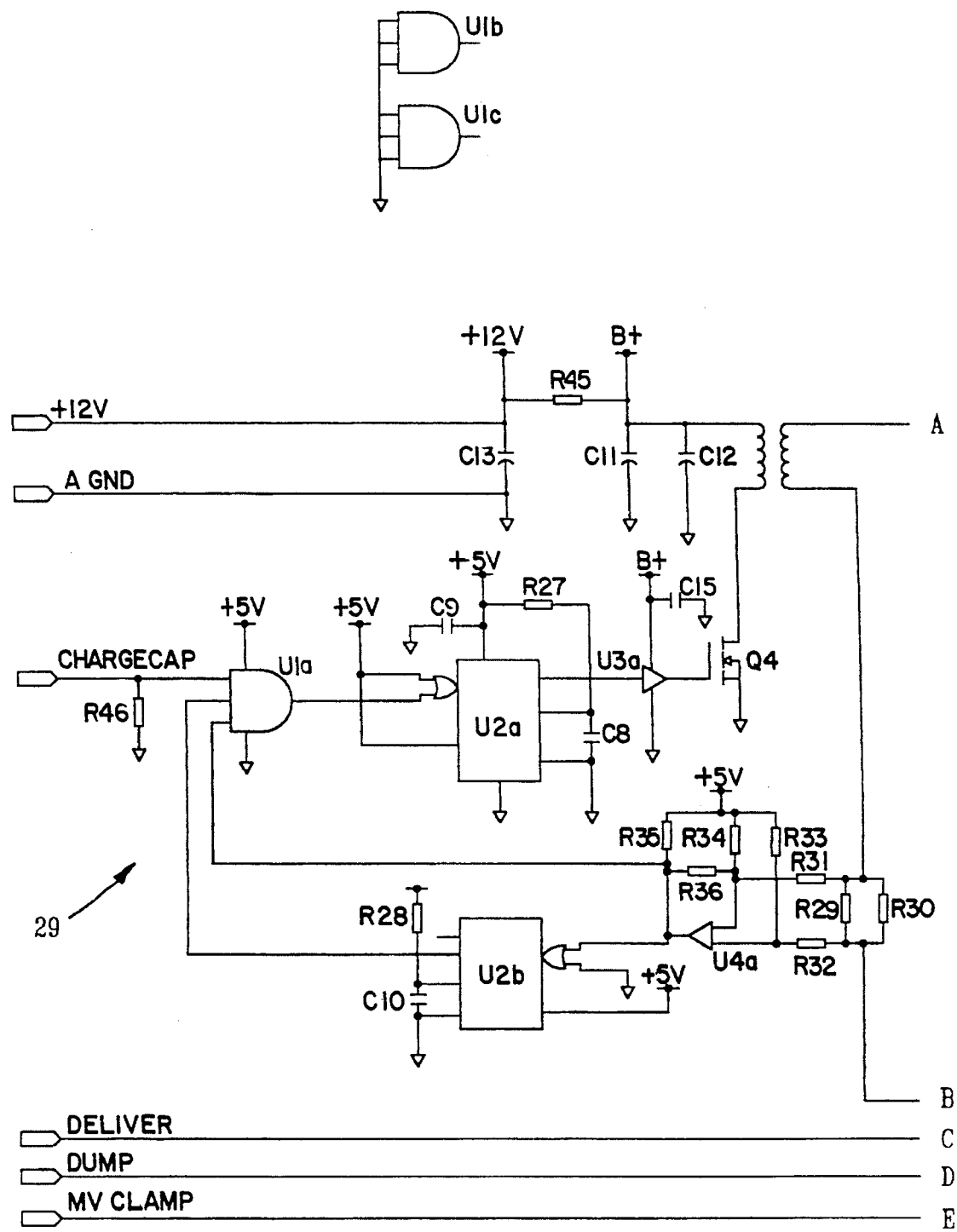

Referring to FIG. 3, the most preferred circuit embodiment 28 of this invention basically comprises a voltage converter circuit 29, six capacitors C1-6 connected in parallel with one another with respect to HV OUT "+" and "–". Seven diodes D1-7 are connected in series, each between first electrodes of the capacitors C1-6. First semiconductor switches Q1, Op1, 2, 3, and 4 are connected in series, each between second electrodes of adjacent capacitors C1-6. The first semiconductor switches OP1, 2, 3, and 4 are shown to be optocoupled transistors, and Q1 is a conventional FET. Second semiconductor switches SCR1, 3, 5, 7, 9 and 11 are connected between the first and second electrodes of adjacent capacitors C. Second switches SCR 1, 3, 5, 7, 9 and 11 are shown to be magnetically triggered SCR's. As was previously discussed, the essential characteristic in the behavior of this circuit 28 is that the capacitors C1-6 charge in parallel via closure of first switches Q1, Op1, 2, 3, and 4, and discharge in series via closure of second switches SCR1, 3, 5, 7, 9 and 11. Switch Op5 is used to shunt any leakage currents. Specifically, switch OP5 is used to shunt leakage current which may come from switch SCR 11. Since switches OP5, 4, 3, 2, 1 and Q1 all operate simultaneously, any leakage currents from switch SCR 11 will be shunted to ground, and the resulting voltage at the cathode of switch SCR 11 will be very low. Therefore, SCR 13 will have essentially zero volts across it, so that any leakage current to the patient through switch SCR 13 will be minimized.

Capacitor C1 preferably has a resistor R1 and an inductor L1 (combination RL1) disposed in series with it. The remaining capacitors C2-6 are similarly configured with RL networks to limit peak current and rise time in switches SCR1, 3, 5, 7, 9 and 11 during an output, or switches SCR2, 4, 6, 8, 10 and 12 during a dump. Clamp diodes D7, 8, 9, 10, 11 and 12 are also shown disposed with respect to these capacitors. Finally, switches SCR2, 4, 6, 8, 10,and 12 are shown disposed in parallel across capacitor networks C1-6, respectively, to dump charge at a predetermined time in the discharge cycle. Preferably, switches SCR2, 4, 6, 8, 10 and 12 are magnetically triggered SCR's.

SCR 13 is shown disposed at the final node anterior to HV Out(+) to prevent leakage of DC current upon capacitor charge up. SCR 13 is triggered simultaneously with SCR1, 3, 5, 7, 9 and 11 and serves as a redundant switch to minimize leakage currents to the patient when capacitors are charged. Specifically, second switch SCR 13 is a redundant output switch which is turned "on" at the same time as the preceding second switches SCR 1, 3, 5, 7, 9 and 11. At all times except during output, all of the switches SCR 1, 3, 5, 7, 9, 11 and 13 are "on". Therefore, any leakage currents out of switch SCR 11 is shunted to ground through switches Q1, and OP1, 2, 3 and 4. As a result, SCR 13 has essentially no voltage across it. Therefore minimal leakage current to the patient occurs.

Circuit section 30 provide a means to clamp the full output voltage in the event of a failure of one of the switches SCR 1, 3, 5, 7, 9 or 11. Circuit section 30 is shown to be connected between switch SCR 11 and switch SCR 13 and comprises a comparator U4 which is connected to the microprocessor via line HV FAULT. The section 30 measures the voltage before switch SCR 13 to make sure it is at or near zero at all times except during discharge. If the voltage rises above this level, the circuit is caused to initiate an immediate dump by the microprocessor. For example, if a switch becomes defective, upon charge-up, the voltage before switch SCR 13 increases causing the clamp circuit 30 to flag the microprocessor of the error. The microprocessor then initiates a shut down.

As many changes are possible to the embodiments of this invention utilizing the teachings thereof, the descriptions above, and the accompanying drawings should be interpreted in the illustrative and not the limited sense.

What is claimed is:

1. An external defibrillator high voltage circuit for generating defibrillation pulses, including:

first and second output terminals configured for electrical interconnection to electrodes;

first and second charge supply terminals configured for interconnection to a charging voltage supply;

at least one capacitor for storing electrical energy;

at least one charging switch responsive to charging control signals, for electrically interconnecting each capacitor to the charge supply terminals to charge the capacitor when switched to an electrically closed state;

a plurality of discharging switches responsive to discharge control signals, for electrically interconnecting each capacitor between the first and second output terminals to produce defibrillation pulses when switched to an electrically closed state, wherein the discharging switches include at least two switches interconnected to each other at a leakage shunting node and in a series circuit between one of the capacitors and the second output terminal; and a leakage shunting switch electrically interconnected between the leakage shunting node and the first output terminal, for electrically interconnecting the leakage shunting node to the first output terminal when switched to an electrically closed state and thereby reducing leakage currents through a patient when defibrillation pulses are not being produced, and electrically isolating the leakage shunting node from the first output terminal when defibrillation pulses are produced.

2. The external defibrillator high voltage circuit of claim 1 wherein:

the at least one capacitor includes N capacitors $C_n$ where N is at least 2 and n=1 ... N, for storing electrical energy, each capacitor having first and second terminals;

the at least one charging switch includes a plurality of charging semiconductor switches responsive to charge control signals, for interconnecting the N capacitors in a parallel circuit between the first and second charge supply terminals to charge the capacitors to the charging voltage when switched to an electrically closed state, and electrically isolating the capacitors from each other when switched to an electrically open state;

the plurality of discharging switches includes a plurality of discharging semiconductor switches responsive to discharge control signals, for simultaneously electrically interconnecting the N capacitors in a series circuit between the first and second output terminals to produce defibrillation pulses when switched to an electrically closed state, and electrically isolating the capacitors from each other when switched to an electrically open state, and wherein the two switches interconnected to each other at the leakage shunting node include semiconductor switches interconnected to each other at the leakage shunting node and in a series circuit between the capacitor $C_N$ and the second output terminal; and the leakage shunting switch includes a semiconductor switch.

3. The external defibrillator high voltage circuit of claim 2 and further including:

a charge dump circuit including one or more charge dump semiconductor switches in a charge dump current flow path and responsive to charge dump control signals, for simultaneously discharging each of the capacitors when the charge dump semiconductor switches are switched to an electrically closed state; and a voltage sensing circuit coupled to the leakage shunting node, for detecting the voltage at the leakage shunting node and causing the charge dump semiconductor switches to be switched to the electrically closed state when the detected voltage is greater than a predetermined level.

4. The external defibrillator high voltage circuit of claim 3 wherein the charge dump circuit includes a charge dump semiconductor switch in parallel with each of the capacitors.

5. The external defibrillator high voltage circuit of claim 4 wherein the charge dump semiconductor switches include silicon controlled rectifiers.

6. The external defibrillator high voltage circuit of claim 5 and further including isolation circuits for coupling the charge dump control signals to the charge dump semiconductor switches.

7. The external defibrillator high voltage circuit of claim 3 wherein:

the second terminal of capacitor $C_1$ is electrically coupled to the second charge supply terminal;

the circuit further includes a plurality of diodes, including a diode interconnected between the second terminals of the capacitors $C_n$ and $C_{n+1}$ for each of the N capacitors; and the discharging semiconductor switches include semiconductor switches interconnected between the second terminal of the capacitor $C_n$ and the first terminal of the capacitor $C_{n+1}$ for each of the N capacitors.

8. The external defibrillator high voltage circuit of claim 7 wherein:

the first terminal of capacitor $C_1$ is electrically coupled to the first charge supply terminal; and the plurality of charging semiconductor switches includes a charging semiconductor switch interconnected between the first terminals of the capacitors $C_n$ and $C_{n+1}$ for each of the N capacitors.

9. The external defibrillator high voltage circuit of claim 3 wherein the first charge supply terminal and the first output terminal are common terminals.

10. The external defibrillator high voltage circuit of claim 9 wherein the charging semiconductor switches include field effect transistors.

11. The external defibrillator high voltage circuit of claim 10 and further including isolation circuits for coupling the charge control signals to the charging semiconductor switches.

12. The external defibrillator high voltage circuit of claim 3 wherein the discharging semiconductor switches include silicon controlled rectifiers.

13. The external defibrillator high voltage circuit of claim 12 and further including isolation circuits for coupling the discharge control signals to the discharging semiconductor switches.

14. An external defibrillator high voltage circuit for generating defibrillation pulses, including:

first and second output terminals configured for electrical interconnection to electrodes;

first and second charge supply terminals configured for interconnection to a charging voltage supply;

at least one capacitor for storing electrical energy;

at least one charging switch responsive to charging control signals, for electrically interconnecting each capacitor to the charge supply terminals to charge the capacitor when switched to an electrically closed state;

a plurality of discharging switches responsive to discharge control signals, for electrically interconnecting each capacitor between the first and second output terminals to produce defibrillation pulses when switched to an electrically closed state, wherein the discharging switches include at least two switches interconnected to each other at a leakage shunting node and in a series circuit between one of the capacitors and the second output terminal;

a leakage shunting switch electrically interconnected between the leakage shunting node and the first output terminal, for electrically interconnecting the leakage shunting node to the first output terminal when switched to an electrically closed state and thereby reducing leakage currents through a patient when defibrillation pulses are not being produced, and electrically isolating the leakage shunting node from the first output terminal when defibrillation pulses are produced;

a charge dump circuit including one or more charge dump semiconductor switches in a charge dump current flow path and responsive to charge dump control signals, for simultaneously discharging each of the capacitors when the charge dump semiconductor switches are switched to an electrically closed state; and a voltage sensing circuit coupled to the leakage shunting node, for detecting the voltage at the leakage shunting node and causing the charge dump semiconductor switches to be switched to the electrically closed state when the detected voltage is greater than a predetermined level.

15. The external defibrillator high voltage circuit of claim 14 wherein the charge dump circuit includes a charge dump semiconductor switch in parallel with each capacitor.

16. The external defibrillator high voltage circuit of claim 15 wherein each charge dump semiconductor switch includes a silicon controlled rectifier.

17. The external defibrillator high voltage circuit of claim 15 and further including an isolation circuit for coupling the charge dump control signals to each charge dump semiconductor switch.

18. The external defibrillator high voltage circuit of claim 14 wherein the first charge supply terminal and the first output terminal are common terminals.

19. The external defibrillator high voltage circuit of claim 14 wherein each charging semiconductor switch includes a field effect transistor.

20. The external defibrillator high voltage circuit of claim 19 and further including an isolation circuit for coupling the charge control signals to each charging semiconductor switch.

21. The external defibrillator high voltage circuit of claim 14 wherein each discharging semiconductor switch includes a silicon controlled rectifier.

22. The external defibrillator high voltage circuit of claim 21 and further including an isolation circuit for coupling the discharge control signals to each discharging semiconductor switch.

* * * * *

UNITED STATES PATENT AND TRADEMARK OFFICE
CERTIFICATE OF CORRECTION

PATENT NO. : 5,601,610
DATED : February 11, 1997
INVENTOR(S) : Eric Persson

It is certified that error appears in the above-indentified patent and that said Letters Patent is hereby corrected as shown below:

Col. 2, line 51, delete one of the ".";

Col. 3, line 14, insert a second quotation mark after the word "on" therefore;

Col. 3, line 31, delete (an) and insert -- (a-n) -- therefore;

Col. 3, line 32, delete S2 (a-n) and insert -- S2(a-n) -- therefore;

Col. 4, line 13, delete "Op1" and insert -- OP1 -- therefore;

Col. 4, line 23, delete "Op1" and insert -- OP1 -- therefore; and

Col. 4, line 40, delete "10,and" and insert -- 10, and -- therefore.

Signed and Sealed this

Seventeenth Day of June, 1997

*Attest:*

BRUCE LEHMAN

*Attesting Officer*  *Commissioner of Patents and Trademarks*